(12) United States Patent
Upmeier et al.

(10) Patent No.: US 12,399,176 B2
(45) Date of Patent: Aug. 26, 2025

(54) METHODS FOR REDUCING INTERFERENCES

(71) Applicant: Roche Diagnostics Operations, Inc., Indianapolis, IN (US)

(72) Inventors: Barbara Upmeier, Iffeldorf (DE); Toralf Zarnt, Penzberg (DE); Johannes Polz, Murnau (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 693 days.

(21) Appl. No.: 17/482,700

(22) Filed: Sep. 23, 2021

(65) Prior Publication Data

US 2022/0057393 A1  Feb. 24, 2022

Related U.S. Application Data

(60) Division of application No. 15/621,280, filed on Jun. 13, 2017, now Pat. No. 11,156,610, which is a continuation of application No. PCT/EP2015/080176, filed on Dec. 17, 2015.

(30) Foreign Application Priority Data

Dec. 18, 2014 (EP) ..................................... 14198784

(51) Int. Cl.
 *G01N 31/00* (2006.01)
 *G01N 33/53* (2006.01)
 *G01N 33/543* (2006.01)
 *G01N 33/68* (2006.01)

(52) U.S. Cl.
 CPC . *G01N 33/54393* (2013.01); *G01N 33/54306* (2013.01); *G01N 33/6854* (2013.01); *G01N 2800/26* (2013.01)

(58) Field of Classification Search
 None
 See application file for complete search history.

(56) References Cited

U.S. PATENT DOCUMENTS

| | | | | |
|---|---|---|---|---|
| 4,444,879 A * | 4/1984 | Foster | ................ | G01N 33/6854 435/805 |
| 5,863,720 A | 1/1999 | Tedder | | |
| 6,127,130 A | 10/2000 | Brizzolara | | |
| 11,156,610 B2 * | 10/2021 | Upmeier | .......... | G01N 33/54393 |
| 2009/0104632 A1 * | 4/2009 | Konrath | ........... | G01N 33/54393 435/7.92 |

FOREIGN PATENT DOCUMENTS

| | | |
|---|---|---|
| CN | 1892223 A | 1/2007 |
| EP | 0404097 A2 | 12/1990 |
| EP | 1683872 A1 | 7/2006 |
| JP | H01-088369 | 6/1989 |
| JP | 2009-513940 A | 4/2009 |
| WO | 1993001161 A1 | 1/1993 |
| WO | 2004059320 A1 | 7/2004 |
| WO | 2006118647 A1 | 11/2006 |
| WO | 2009513940 A1 | 4/2009 |
| WO | 2010075475 A1 | 7/2010 |
| WO | 2013092611 A1 | 6/2013 |
| WO | 2014195899 A1 | 12/2014 |

OTHER PUBLICATIONS

Mitrunen, K et al. "Dual-label one-step immunoassay for simultaneous measurement of free and total prostate-specific antigen concentrations and ratios in serum." Clinical chemistry vol. 41,8 Pt 1 (1995): 1115-20. (Year: 1995).*
Feng, Da-Fei and Doolittle, Russell F ., Progressive Sequence Alignment as a Prerequisite to Correct Phylogenetic Trees, Journal of Molecular Evolution, 1987, pp. 351-360, vol. 25.
Higgins, D. G. and Sharp, P. M., Fast and sensitive multiple sequence alignments on a microcomputer, Computer Applications in the Biosciences: CABIOS, 1989, pp. 151-153, vol. 5, Abstract only.
Holliger, Philipp et al., "Diabodies": Small bivalent and bispecific antibody fragments, Proceedings of the National Academy of Sciences USA, 1993, pp. 6444-6448, vol. 90.
Hudson, Peter J. and Souriau, Christene, Engineered antibodies, Nature Medicine, 2003, pp. 129-134, vol. 9, No. 1.
International Search Report issued Feb. 18, 2016, in Application No. PCT/EP2015/080176, 4 pages.
Needleman, Saul B. and Wunsch, Christian D., A General Method Applicable to the Search for Similarities in the Amino Acid Sequence of Two Proteins, Journal of Molecular Biology, 1970, pp. 443-453, vol. 48.
Park, Jason Y. and Kricka, Larry J., Interferences in Immunoassay, The Immunoassay Handbook, 2013, pp. 103-416, Elsevier Ltd.
Schiettecatte, Johan et al., Interferences in Immunoassays, Advances in Immunoassay Technology, InTech, JQ12, pp. 45-63, Norman H. L. Chiu, Editor.
Smith, Temple F. and Waterman, Michael S., Comparison of Biosequences, Advances in Applied Mathematics, 1981, pp. 482-489, vol. 2.
ISA/EP, Written Opinion issued in corresponding Application No. PCT/EP2015/080176, dated Feb. 18, 2016, 6 pp.

(Continued)

*Primary Examiner* — Lisa V Cook
(74) *Attorney, Agent, or Firm* — Taft Stettinius & Hollister LLP

(57) ABSTRACT

A method for determining an analyte in a sample suspected to comprise the analyte, includes a) contacting with said sample at least a first and a second capture compound for the analyte; b) contacting the capture compounds contacted with the sample with a specifier; c) determining the amount of complexes comprising the specifier and a capture compound; and d) determining the analyte in a sample based on the result of step c). Additionally, a method for improving the specificity of an indirect immunoassay for determining an analyte, kits, devices, and uses related to the aforementioned methods are also disclosed.

20 Claims, 6 Drawing Sheets
Specification includes a Sequence Listing.

(56) References Cited

OTHER PUBLICATIONS

European Patent Office, International Preliminary Report on Patentability issued in corresponding Application No. PCT/EP2015/080176, dated Mar. 9, 2017, 16 pp.

"Core/HBcAg," GenBank Accession No. Q17UT2, URL: https://www.ncbi.nim.nih.gov/protein/Q17UT2, Accessed on Mar. 25, 2025.

"RecName: Full=Capsid protein; AltName: Full=Core antigen; AltName: Full=Core protein; AltName: Full=HBcAg; AltName: Full=p21.5," GenBank Accession No. P03147, URL: https://www.ncbi.nlm.nih.gov/protein/P03147/, Accessed on Mar. 25, 2025.

"RecName: Full=Capsid protein; AltName: Full=Core antigen; AltName: Full=Core protein; AltName: Full=HBcAg; AltName: Full=p21.5," GenBank Accession No. P03148, URL: https://www.ncbi.nlm.nih.gov/protein/P03148, Accessed on Mar. 25, 2025.

"RecName: Full=Capsid protein; AltName: Full=Core antigen; AltName: Full=Core protein; AltName: Full=HBcAg; AltName: Full=p21.5," GenBank Accession No. P03149, URL: https://www.ncbi.nlm.nih.gov/protein/P03149, Accessed on Mar. 25, 2025.

"Capsid protein [Hepatitis B virus]," GenBank Accession No. NP_647607, Url: https://www.ncbi.nlm.nih.gov/protein/NP_647607.1?report=genpept, Accessed on Mar. 25, 2025.

"Hepatitis B virus, complete genome," GenBank Accession No. AY123424, URL: https://www.ncbi.nlm.nih.gov/nuccore/AY123424, Accessed on Mar. 25, 2025.

Dowdy et al., "Statistics for Research," Third Edition, Wiley Series in Probability and Statistics, A John Wiley & Sons, Inc. Publication, 2004, 634 pp.

* cited by examiner

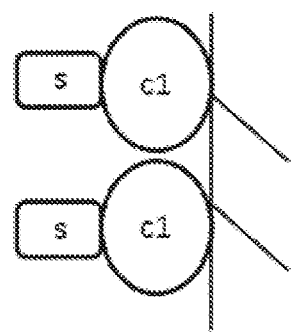
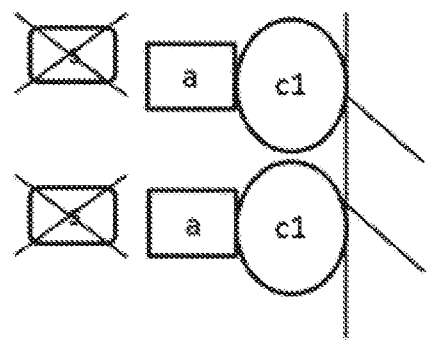

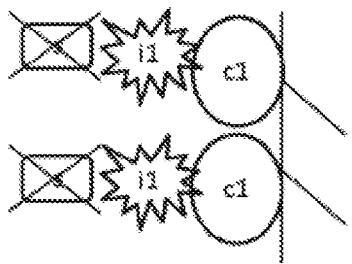
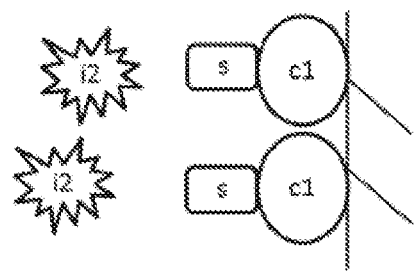

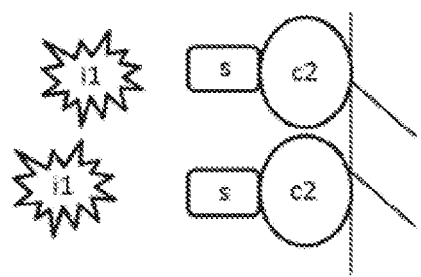

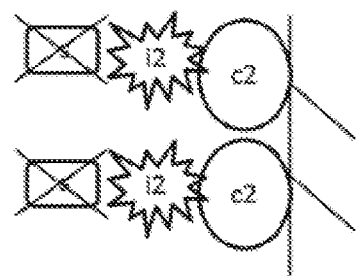

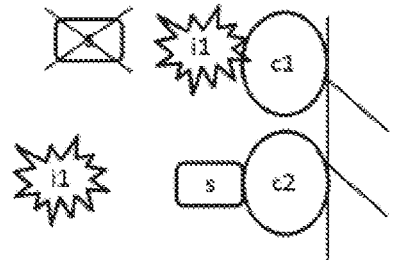

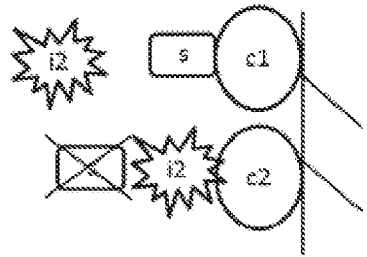

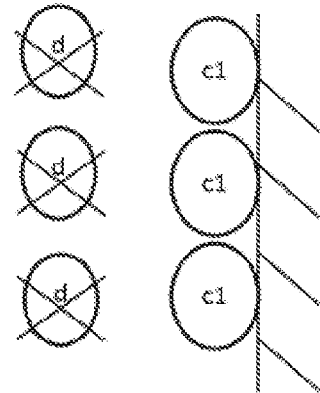

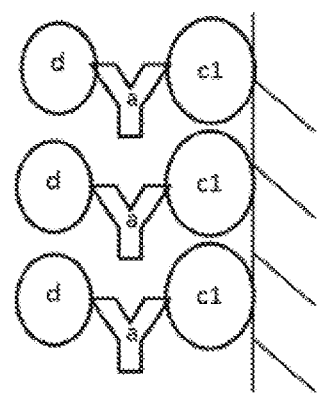

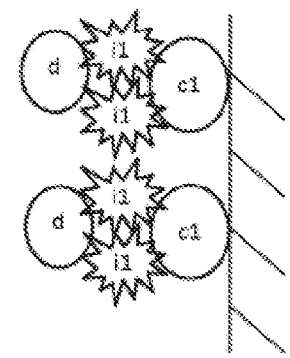

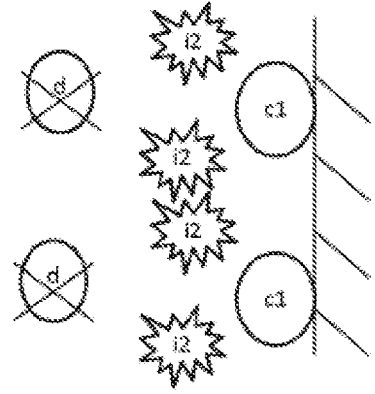

SEQUENCE LISTING

<160> NUMBER OF SEQ ID NOS: 2

<210> SEQ ID NO 1
<211> LENGTH: 185
<212> TYPE: PRT
<213> ORGANISM: Hepatitis B virus

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 2
<211> LENGTH: 183
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

METHODS FOR REDUCING INTERFERENCES

CROSS-REFERENCE TO RELATED APPLICATIONS

This application is a divisional of U.S. patent application Ser. No. 15/621,280, filed Jun. 13, 2017, which issued as U.S. Pat. No. 11,156,610 on Oct. 26, 2021, which is a continuation of International Application No. PCT/EP2015/080176 filed Dec. 17, 2015, which claims priority to European Application No. 14198784.2 filed Dec. 18, 2014, the disclosures of which are hereby incorporated by reference in their entirety.

STATEMENT IN SUPPORT FOR FILING A SEQUENCE LISTING

A paper copy of the Sequence Listing and a computer readable form of the Sequence Listing containing the file named "P32280-US-1_Sequence_Listing_ST25.txt", which is 3,709 bytes in size (as measured in MICROSOFT WINDOWS® EXPLORER), are provided herein and are herein incorporated by reference. This Sequence Listing consists of SEQ ID NOs:1-2.

FIELD OF THE INVENTION

The present invention relates to a method for determining an analyte in a sample suspected to comprise said analyte, comprising a) contacting with said sample at least a first and a second capture compound for said analyte, wherein said first and second capture compounds are non-identical capture compounds, and wherein said capture compounds compete in binding to said analyte; b) contacting said capture compounds contacted with said sample with a specifier, wherein said specifier competes in binding to said capture compounds with said analyte; c) determining the amount of complexes comprising said specifier and a capture compound; and d) determining said analyte in a sample based on the result of step c). The present invention further relates to a method for improving the specificity of an indirect immunoassay for determining an analyte, comprising replacing at least 10% of a capture compound by a non-identical capture compound; wherein the capture compound replaced competes in binding to said analyte with the capture compound introduced. The present invention further relates to kits, devices, and uses related to the aforementioned methods.

BACKGROUND

Laboratory tests, in particular immunological tests, have become invaluable tools in the diagnosis of disease. Immunoassays in particular have provided the possibility to specifically detect single analytes or groups of analytes in complex mixtures, e.g. body fluids, such as blood or plasma. However, several causes of interference in immunoassays have been identified, e.g. cross-reactivity of an interfering substance with a capture compound, unspecific binding of detector compound to a solid phase, "bridge" binding of capture compound and detector compound by heterophile antibodies or, in particular, human anti-mouse antibodies (HAMA), to name a few (see, e.g. Park & Kricka (2013), Ch. 5.3-Interferences in Immunoassay, in The Immunoassay Handbook (Fourth Edition), edited by David Wild, Elsevier, Oxford: 403; Schiettecatte (2012), Interferences in Immunoassays, Advances in Immunoassay Technology, Dr. Norman H. L. Chiu (Ed.)).

In competitive immunoassays, analytes comprised in a sample compete with a labeled analyte (specifier) for binding to a capture compound, which is frequently an antibody, or, in case the presence of antibodies to e.g. a pathogenic agent is to be tested in a serum sample, an antigen of said pathogenic agent. In case the concentration of analyte in the sample is high, there is a strong competition, leading to a decreased binding of the specifier to the capture compound, causing signal reduction, which, depending on the test format, leads to a quantitative or qualitative test result. It is a disadvantage of the immunoassays known in the art that antigens used as a capture compound may also be bound by interfering compounds from the sample. These interfering compounds compete with the specifier for binding epitopes of the capture compound. Depending on how severe the competition is, false test results are possible, causing a decrease of the specificity of the respective immunoassay. This decrease in specificity can be especially pronounced if complex capture compounds, potentially even consisting of several subunits with a large number of conformational epitopes, e.g. viral capsids, are used. In such cases, the classical methods of interference elimination, e.g. addition of alternative targets for the interfering compounds, may be inefficient.

In non-competitive immunoassays, the analyte is detected by contacting the analyte to a compound specifically binding to the analyte and either carrying a label itself or being target of a second molecule carrying a label. Thus, in non-competitive immunoassays, the amount of analyte is determined by determining the amount of complexes formed between the analyte and a detector compound carrying a label. Accordingly, the analogous specificity problems may be faced as described above.

Antigens being immunologically only slightly different (e.g. by a production in a different expression system, different amino acid sequence, difference in glycosylation, differences in purification and refolding procedures, as well as differences in buffer and storage conditions) have an individual scope of interferences. Accordingly, samples leading to a false result in an immunoassay with antigen X1 may provide correct results in a test with antigen X2 and vice versa. Accordingly, exchanging an antigen for a different antigen frequently does not lead to an improvement of specificity, but only to a change of the scope of samples leading to false results.

Problem to be Solved

It is therefore an objective of the present invention to provide improved immunoassays avoiding the problems as described above.

SUMMARY OF THE INVENTION

These problems are solved by the methods, kits, devices, and compositions with the features of the independent claims. Typical embodiments, which might be realized in an isolated fashion or in any arbitrary combination are listed in the dependent claims.

The present invention relates to a method for determining an analyte in a sample suspected to comprise said analyte, comprising a) contacting with said sample at least a first and a second capture compound for said analyte, wherein said first and second capture compounds are non-identical capture compounds, and wherein said capture compounds compete in binding to said analyte; b) contacting said capture compounds contacted with said sample with a specifier, wherein said specifier competes in binding to said capture compounds with said analyte; c) determining the amount of complexes comprising said specifier and a capture compound; and d) determining said analyte in a sample based on the result of step c). The present invention further relates to a method for improving the specificity of an indirect immunoassay for determining an analyte, comprising replacing at least 10% of a capture compound by a non-identical capture compound; wherein the capture compound replaced competes in binding to said analyte with the capture compound introduced. The present invention further relates to kits, devices, and uses related to the aforementioned methods.

DETAILED DESCRIPTION OF THE INVENTION

The present invention relates to a method for determining an analyte in a sample suspected to comprise said analyte, comprising
- a) contacting with said sample at least a first and a second capture compound for said analyte, wherein said first and second capture compounds are non-identical capture compounds, and wherein said capture compounds compete in binding to said analyte;
- b) contacting said capture compounds contacted with said sample with a specifier, wherein said specifier competes in binding to said capture compounds with said analyte;
- c) determining the amount of complexes comprising said specifier and a capture compound; and
- d) determining said analyte in a sample based on the result of step c).

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention. The term "about" in the context of specific values or ratios of the present invention refers to said value or ratio +/−30%, +/−20%, +/−10%, or, in an embodiment +/−5% of a given value or ratio.

The method of the present invention, in an embodiment, is an in vitro method. Moreover, it may comprise steps in addition to the ones specifically mentioned. In particular, step b) may comprise steps of providing a sample, or step c) may comprise addition of further compounds in order to facilitate binding and detection. Furthermore, some or all steps may be assisted by automated equipment.

As used herein, the term "determining" refers to determining at least one immunological feature of an analyte to be determined by the method of the present invention in the sample. Immunological features in accordance with the present invention, in an embodiment, are structural features of the analyte facilitating detection of the analyte in a sample by immunological means. In an embodiment, said immunological features facilitate identification, in a further embodiment, quantification of the analyte by immunological means. Accordingly, typical immunological features are features facilitating differentiation of said analyte from other chemical compounds in a sample. In an embodiment, determining an analyte is establishing whether an analyte is present or absent in the sample at a concentration above the detection limit of the method. Methods of determining a detection limit are known to the skilled person. In a further embodiment, determining is determining semi-quantitatively or quantitatively the amount or concentration of an analyte in a sample. For quantitative determination, either the absolute or precise amount of the analyte will be determined or the relative amount of the analyte will be determined. The relative amount may be determined in a case were the precise amount of an analyte can or shall not be determined. In said case, it can be determined whether the amount in which the analyte is present is increased or diminished with respect to a second sample comprising said analyte in a second amount.

As will be understood by the skilled person, there will typically be no requirement to determine the first capture compound/analyte and second capture compound/analyte complexes separately. Thus, in an embodiment, the complexes of first capture compound and analyte and of the second capture compound and analyte are determined together, i.e. indiscriminative between said first and said second capture compound. Thus, in an embodiment, the total amount of analyte present in a complex with either the first capture compound or the second capture compound is determined.

As will be further understood by the skilled person, the determination of analyte/capture compound complexes will depend on the assay format chosen. In an embodiment, the assay is a competitive immunoassay, typically a competitive, heterogeneous immunoassay, i.e. an immunoassay, wherein an analyte competes with a labeled derivative of said analyte for binding to a capture compound bound to a solid surface, and wherein the amount of labeled derivative of said analyte bound to said capture compound is determined. In an embodiment, the competitive assay is an assay for Anti-HBc, Anti-HAV (anti-Hepatitis A virus), Anti-HBe (anti-Hepatitis B e-antigen), Folate, Folate RBC (red blood cell), Anti-TSH-R, Vitamin D total, Vitamin B12, Tyroxin T4, FT 4 (free thyroxine), Tyroxin T3, FT 3 (free triiodothyronine), Testosteron, Progesterone, Digitoxin, Anti-TG, Anti-TPO (anti-Thyroid peroxidase), DGEA, or Estradiol. In a further embodiment, the immunoassay is a double-antigen sandwich assay ("DAGS") wherein a bivalent analyte, e.g. an antibody, is bound to a capture compound bound to a solid surface, and wherein the amount of analyte/capture compound complexes is determined by binding of a detector compound as specified herein below to said analyte/capture compound complexes. In an embodiment, the DAGS assay is an assay for Anti-Toxoplasma IgG, Anti-rubella IgG, Anti-HBs 1G, HCV (hepatitis C virus), e.g. HCVII, CMV (cytomegalovirus) IgG, Syphilis, HTLV (Human T-cell lymphotropic virus), or Chagas (American trypanosomiasis).

The term "biological molecule" is known to the skilled person and, typically, relates to a molecule produced by the metabolism of at least one organism. Accordingly, the term "biological macromolecule" relates to a polymer produced by an organism, in an embodiment, from monomeric precursors. A typical biological macromolecule is a polypeptide, DNA, RNA, or a polysaccharide.

The term "analyte", as used herein, relates to a chemical molecule, in an embodiment, an organic molecule, binding to the capture compound and/or detector compound of the present invention with sufficient affinity to allow detection of an analyte/capture compound and/or detector compound complex. In an embodiment, the dissociation constant ($K_d$) of the analyte/ligand complex is at most $10^{-7}$ mol/L, in a further embodiment, at most $10^{-8}$ mol/1, in a further embodiment, at most $10^{-9}$ mol/L. In an embodiment, the dissociation constant of the complex formed between the first capture compound of the invention and the analyte and the dissociation constant of the complex formed between the second capture compound of the invention and the analyte are different by not more than a factor of five; in an embodiment by no more than a factor of two; in a further embodiment by no more than a factor of 1.5. In an embodiment, the dissociation constant of the complex formed between the first capture compound and the analyte has a value of from 70% to 130% of the dissociation constant of the complex formed between the second capture compound and the analyte. In a further embodiment, the dissociation constant of the complex formed between the first capture compound and the analyte has a value of from 80% to 120% of the dissociation constant of the complex formed between the second capture compound and the analyte. In a further embodiment, the dissociation constant of the complex formed between the first capture compound and the analyte has a value of from 90% to 110% of the dissociation constant of the complex formed between the second capture compound and the analyte. In a further embodiment, the dissociation constant of the complex formed between the first capture compound and the analyte and the dissociation constant of the complex formed between the second capture compound and the analyte are essentially equal or are equal. In an embodiment, the analyte has a molecular mass of at least 100 (corresponding to 100 atomic mass units, and to 100 Da; 1 Da corresponding to $1.66 \times 10^{-27}$ kg), in a further embodiment, at least 250, in a further embodiment, at least 500, or, in a further embodiment, at least 1000. In an embodiment, the analyte is a biological molecule, in a further embodiment, the analyte is a biological macromolecule. In a further embodiment, the analyte is a polypeptide.

In an embodiment, in case the analyte of the present invention is a polypeptide, the polypeptide is an antigen produced by an infectious agent, e.g., a virus or bacterium, or an antibody, e.g., an antibody produced by a subject against an antigen produced by an infectious agent. In an embodiment, the analyte is a polypeptide, in a further embodiment, an antibody against a viral antigen, in a further embodiment, against a viral polypeptide, or, in a further embodiment, against a viral capsid polypeptide. In an embodiment, the viral capsid polypeptide is a Hepatitis virus capsid polypeptide, in an embodiment, a Hepatitis B virus (HB) capsid polypeptide, or, in a further embodiment, a HB core (HBc) antigen. Accordingly, the analyte, in an embodiment, is an antibody against a Hepatitis virus capsid polypeptide, e.g., against a Hepatitis B virus (HB) capsid polypeptide, typically, against a HB core (HBc) antigen or a HBe antigen. In an embodiment, the first capture compound is HBc antigen as shown in Genbank Acc No: Q17UT2 GI:123867942 (SEQ ID NO: 1). In a further embodiment, the first capture compound is HBc antigen as shown in Genbank Acc No: Q17UT2 GI:123867942 (Hepatitis B virus subtype adw2 core antigen, SEQ ID NO: 1) and the second capture compound is HBc antigen as shown in Genbank Acc No. P03147.1 GI:116947 (Hepatitis B virus genotype D subtype adw core antigen, SEQ ID NO: 2). In a further embodiment the first and second capture compounds are HBc antigen sequences selected from HBc antigen sequences known in the art such as HBcAg protein sequences identified by their Genbank Acc. Nos: P03148.3 GI:166215076, P03149.1 GI:116945, NP_647607.1 GI:21326588, and AY123424.1 GI:22203511.

In an embodiment, to facilitate cloning, the N- and/or the C-terminal end of each HBV core antigen sequence may be shortened by deleting 1 to 5 of the N- and/or C-terminal amino acids of said antigen sequence. In a further embodiment, tags comprising 2 to 15 amino acids can be added to either the N-terminal or the C-terminal end or to both ends of the antigen without interfering with the antigenic properties of the HBV core antigen.

The term polypeptide, as used herein, in an embodiment, includes variants and fragments of the specifically indicated polypeptides. Variants include polypeptides comprising amino acid sequences which are at least 70%, at least 75%, at least 80%, at least 85%, at least 90%, at least 95%, at least 98% or at least 99% identical to the amino acid sequences specifically indicated, e.g. shown in SEQ ID NO: 1 or 2. The percent identity values are, preferably, calculated over the entire amino acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970)) and Smith and Waterman (Adv. Appl. Math. 2; 482-489 (1981))], which are part of the GCG software packet [Genetics Computer Group, 575 Science Drive, Madison, Wisconsin, USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polypeptide comprising a fragment of any of the aforementioned polypeptide sequences, in an embodiment, is also encompassed as a polypeptide of the present invention. The fragment be a polypeptide which still has the of being a capture compound or a detector compound as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive amino acid residues of any one of the aforementioned amino acid sequences comprising at least 20, at least 30, at least 50, at least 80, at least 100 or at least 150 consecutive amino acids of any one of the aforementioned amino acid sequences.

The polypeptides of the present invention either essentially consist of the aforementioned amino acid sequences or comprise the aforementioned amino acid sequences. Thus, they may contain further polypeptide sequences as well. Specifically, the polypeptides of the present invention may be fusion proteins wherein one partner of the fusion protein is a polypeptide as recited above. Such fusion proteins may comprise as additional part other enzymes of the fatty acid or lipid biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes or for binding said polypeptides to a solid surface. Tags for the different purposes are well known in the art and comprise FLAG-tags, 6-histidine-tags, MYC-tags, Biotin, and the like.

It is, however, also envisaged that the analyte is a low-molecular weight compound determinable by complex formation with a capture compound, including, e.g. thyroxin (T4), triiodothyronine (T3), folic acid, folic acid binding protein, vitamin Bu, intrinsic factor, and the like.

As used herein, the term "capture compound" relates to a chemical molecule binding, directly or indirectly, to the analyte of the present invention as specified herein above, and bound to a solid surface or adapted to be bound to a solid surface.

In an embodiment, the capture compound is an organic molecule, in a further embodiment, a biological macromolecule as specified herein above, e.g., a polypeptide as specified herein above. In an embodiment, the capture compound binds indirectly to the analyte of the present invention with sufficient affinity to allow detection of the complex comprising analyte and capture compound; i.e., in such case, the capture compound is an indirect ligand. The term "indirect binding", as used herein, relates to a binding wherein the ligand does not directly contact the analyte, but contacts a chemical molecule binding the analyte, in an embodiment specifically binding the analyte, wherein, in an embodiment, said molecule binding the analyte is a molecule directly binding the analyte, i.e. is a direct ligand. Accordingly, in an embodiment, the analyte, a chemical molecule binding the analyte, and the indirect ligand form a complex with the properties as indicated above, in particular with the dissociation constants as indicated. As will be understood by the skilled person, the definition of the term "compete in binding" applies mutatis mutandis to the indirect ligands of the present invention, i.e. the indirect ligands, in an embodiment, have the property of being unable to bind to said molecule binding the analyte at the same time. In a further embodiment, the capture compound directly binds to the analyte of the present invention with sufficient affinity to allow detection of the analyte/capture compound complex, as specified herein above. Accordingly, in an embodiment, the capture compound is a direct ligand.

According to the present invention, at least a first and a second capture compound are provided, wherein said first and second capture compounds are non-identical capture compounds. As used herein, the term "non-identical" capture compounds relates to two or more species of capture compound molecules measurably different in at least one chemical and/or physical property. Typically, said least one chemical and/or physical property is not an indicator and is not a property related to binding of said capture compound to a solid surface. Typical properties are amino acid sequence, glycosylation, three-dimensional folding and/or conformation, and length of polypeptide chain. However, also differences in the concentration and/or identity of impurities in two preparations of the same capture compound are contemplated by the present invention. Accordingly, in an embodiment, a second capture compound is derived or derivable from a first capture compound by at least one of (i) introducing at least one amino acid exchange into the amino acid sequence of said first capture compound, (ii) producing said second capture compound in a different cellular background as compared to said first capture compound, (iii) removing or preventing glycosylation of said second capture compound as compared to said first capture compound, (iv) purifying said second capture compound by different means as compared to said first capture compound, (v) denaturing and/or refolding said second capture compound under different conditions as compared to said first capture compound, and (vi) storing said second capture compound under different conditions as compared to said first capture compound. In an embodiment, said first and second capture compounds are antibodies recognizing essentially the same epitope and said second capture compound is a variant of an antibody being the first capture compound. In a further embodiment, at least one of said first and second capture compounds is not an antibody. In an another embodiment, said first and second capture compounds are not antibodies.

According to the present invention, at least a first and a second capture compound are provided, wherein said capture compounds compete in binding to said analyte. As used herein, the term indicating that two compounds "compete in binding" to an analyte relates to the property of molecules of said compounds of being unable to bind to essentially the same binding site of said analyte at the same time. Thus, typically, in case two capture compounds compete in binding to an analyte and in case said analyte has one binding site for said capture compounds, at each point in time, only one molecule of said capture compounds can be bound to said analyte. It will be understood by the skilled person that the above applies mutatis mutandis in case the analyte has two or more binding sites for the capture compounds. The skilled person knows how to determine competition in binding. In an embodiment, competing in binding to an analyte is binding to the same or essentially the same substructure of said analyte. In a further embodiment, in case the analyte is a polypeptide, the epitope bound by a first capture compound and the epitope bound by a second capture compound have at least 3 amino acids, in an embodiment, 3 contiguous amino acids, of the analyte in common. Typically, in such case, the epitope bound by a first capture compound and the epitope bound by a second capture compound have at least 4, 5, 6, or 7 amino acids of the analyte in common.

In an embodiment, the first and second capture compound do not compete in binding to an interfering compound. The term "interfering compound", as used herein, relates to a compound decreasing the specificity of an immunoassay. In an embodiment, the interfering compound is a compound binding to a capture compound of the present invention which is not the analyte.

In an embodiment, the first and the second capture compound are used at a ratio of 1:5 to 5:1, typically 1:2 to 2:1, about 1:1, or 1:1. In a further embodiment, three capture compounds are used at a ratio of about 2:1:1, 1:2:1, or 1:1:2, about 1:1:1, or 1:1:1 Thus, in an embodiment, the first and the second capture compound and potentially present further capture compounds, are present in the reaction mixture in about the same amount, in a further embodiment, in the same amount.

Methods of binding biological molecules, typically polypeptides, to solid surfaces are well known in the art and include, e.g. binding by hydrophobic interaction, biotinylation and binding via immobilized streptavidin, covalent binding, antibody-antigen interaction, and the like, or a combination of these interactions, e.g. antibody-antigen interaction between an antibody and a polypeptide of a pathogen, wherein said antibody is biotinylated and bound to a solid surface via immobilized streptavidin. Accordingly, the capture compound may, preferably, also be a capture complex. In an embodiment, the capture compound is the compound of a capture complex directly binding to the analyte. The skilled person knows how to bind a capture compound or complex to a solid surface, depending on the solid surface selected. In an embodiment, the capture compound is a viral polypeptide, e.g., a viral capsid polypeptide. In an embodiment, said capture compound is a Hepatitis virus capsid polypeptide, in an embodiment, a Hepatitis B virus (HB) capsid polypeptide, e.g., a HB core (HBc) antigen or a HBe antigen. It is, however, also envisaged that the capture compound is an antibody.

The term "antibody", as used herein, includes monoclonal antibodies, multispecific antibodies (e.g. bispecific antibodies) formed from at least two intact antibodies, and antibody fragments so long as they exhibit the desired binding activity as specified elsewhere herein. In an embodiment, an antibody is not an antibody comprised in an antiserum, typically not a polyclonal antibody or a polyclonal serum. Accordingly, in an embodiment, an antibody is an antibody comprised in a mixture wherein at least 80%, in an embodiment at least 90%, in a further embodiment, at least 95% of antibody molecules comprised in said mixture are at least one capture compound or at least one detector compound of the present invention. In an embodiment, the antibody is a monoclonal antibody. In an embodiment, the antibody is a full-length antibody or an antibody fragment.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W. B. Saunders, Co. (2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region. "Antibody fragments" comprise a portion of an intact antibody, in an embodiment, comprising the antigen-binding region thereof. Examples of antibody fragments include Fab, Fab', F(ab')2, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site. The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson et al., Nat. Med. 9 (2003) 129-134; and Hollinger et al., PNAS USA 90 (1993) 6444-6448. Triabodies and tetrabodies are also described in Hudson et al., Nat. Med. 9 (2003) 129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds an analyte, wherein the analyte-binding polypeptide sequence was obtained by a process that includes the selection of a single analyte binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

As used herein, the term "solid surface" relates to any suitable solid surface adapted for binding the capture compound of the present invention and adapted for being separated, e.g., by physical means, from a sample. In an embodiment, said solid surface is a surface of a bead, in an embodiment, a microbead, e.g. a magnetic or paramagnetic microbead. In an embodiment, said surface is adapted to improve binding of the capture compound, e.g. by attaching, covalently or non-covalently, molecules binding a substructure of the capture compound. Typical molecules binding a substructure of the capture compound are, e.g. antibodies, streptavidin, complexed Nickel ions, and the like. In a further embodiment, the solid surface binds said capture compound by covalent or non-covalent bonds, e.g. by hydrophobic interaction. Thus, in an embodiment, said solid surface is a surface of a multi-cluster plate. In an embodiment, the surface of the multi-cluster plate is pretreated to increase affinity and/or capacity for binding of a capture compound. Suitable pretreatments are known in the art.

The term "sample", as used herein, relates to a sample suspected to comprise the analyte of the present invention. In an embodiment, the sample is or comprises a sample of a body fluid, a sample from a tissue or an organ, or a sample of wash/rinse fluid or a swab or smear obtained from an outer or inner body surface. The sample, in an embodiment, comprises at least one analyte as specified elsewhere herein. Samples of blood, plasma, serum, urine, saliva, or lacrimal fluid are encompassed by the method of the present invention. Samples can be obtained by use of brushes, (cotton) swabs, spatula, rinse/wash fluids, punch biopsy devices, puncture of cavities with needles or lancets, or by surgical instrumentation. However, samples obtained by well known techniques including, in an embodiment, scrapes, swabs or biopsies from the urogenital tract, perianal regions, anal canal, the oral cavity, the upper aerodigestive tract and the epidermis are also included as samples of the present invention. Cell-free fluids may be obtained from the body fluids or the tissues or organs by lysing techniques such as homogenization and/or by separating techniques such as filtration or centrifugation. In an embodiment, samples are obtained from body fluids known to comprise HB virus polypeptides or/and antibodies against at least one HB virus polypeptide, i.e., in an embodiment, blood, plasma, serum, saliva, or the like. It is to be understood that the sample may be further processed in order to carry out the method of the present invention. Particularly, cells may be removed from the sample by methods and means known in the art. Moreover, at least one analyte may be extracted and/or purified from the sample by methods and means known in the art. Thus, the term sample also may relate to preparations comprising or suspected to comprise at least one analyte, diluted, enriched, purified and/or extracted from a sample.

In an embodiment, the method of the present invention is a competitive immunoassay. Accordingly, the method further comprises admixing a specifier to a sample. In an embodiment, the method of the present invention is a heterogeneous competitive immunoassay and comprises indirectly determining the amount of complexes formed between an analyte and two non-identical capture compounds by determining the amount of complexes formed between said specifier and said non-identical capture compounds.

The term "contacting" as used in the context of the methods of the present invention is understood by the skilled person. In an embodiment, the term relates to bringing a compound of the present invention in physical contact with a sample or with a further compound and thereby, e.g. allowing the sample and the compound to interact.

The term "specifier" is known to the skilled person and relates to a compound competing with an analyte for binding to the capture compounds, bonded to an indicator. Typically, the specifier is structurally similar to the analyte. Typically, the specifier comprises the substructure of the analyte bound by the capture compounds, bonded to an indicator. In an embodiment, the specifier is a compound comprising the analyte and an indicator as structural elements, or the specifier consists of the analyte covalently bonded to an indicator.

The term "indicator", as used herein, is a compound adapted for making the presence of a molecule or complex comprising said indicator detectable. Typically, the indicator has a detectable property, typically an optical or/and enzymatic property. It is, however, also envisaged that said detectable property is the property of emitting radioactivity.

The term "optical property", as used herein, relates to any property which can be detected by an optical instrument. Specifically, the optically determinable property may be or may comprise at least one property selected from the group consisting of: a reflection property, a transmission property, an emission property, a scattering property, a fluorescence property, a phosphorescence property, a diffraction property, and a polarization property. Further optical properties envisaged by the present invention are color, fluorescence, luminescence, or refraction. In an embodiment, an optically determinable property as referred to herein refers to a property of a chemical compound which can be optically detected such as light absorption, light emission, light remission, or properties associated therewith. It will be understood that detecting an optically determinable property as used herein encompasses the detection of the presence of a property which was not detectable before, the detection of the absence of a property which has been detected before, and the detection of quantitative changes of a property, i.e., the detection of the change of the signal strength which correlates to the extent of the change of the at least one optical property. It is understood that the term "optically determinable property", in an embodiment, also relates to electrochemiluminescence, which is also known as electrogenerated chemiluminescence.

The term "enzymatic property", as used herein, relates to a property of an indicator of producing a detectable product from a substrate by means of biological catalysis. Accordingly, an enzymatic property is typically conferred by the presence of a polypeptide having said enzymatic property in said indicator. Typically, the enzymatic property is at least one enzymatic activity selected from the group consisting of: phosphatase activity (e.g. in alkaline phosphatase), peroxidase activity (e.g. in horseradish peroxidase), and glycosidase activity (e.g. in beta-galactosidase). Typical substrates for enzymatic activities are well-known in the art. Typically, said enzymatic activity produces a product having a determinable optical property as specified herein above, or/and said enzymatic activity produces a product being determinable by an electrical instrument.

In an embodiment, the method of the present invention is a double-antigen sandwich assay ("DAGS"). Accordingly, the method further comprises detecting complexes formed between said analyte and said capture compound by (i) contacting said complexes with at least one detector compound and (ii) determining the amount of ternary complexes comprising said analyte, said capture compounds, and said detector compounds.

In the embodiment of a DAGS assay, a detector compound is used. The term "detector compound", as used herein, relates to a chemical molecule binding, directly or indirectly, to the analyte of the present invention as specified herein above, and bonded to an indicator as specified elsewhere herein. In an embodiment, the detector compound is not bound to a solid surface and not adapted to be bound to a solid surface. As will be understood by the skilled person, the detector compound may also be an indirect detector compound, i.e. a detector compound not contacting the analyte directly, as specified herein above for the ligand of the invention. In an embodiment, the detector compound is a direct detector compound. Accordingly, in an embodiment, the definitions provided above for the capture compounds of the present invention, in as far as they do not relate to binding of the compounds to a solid surface, apply to the detector compounds of the present invention mutatis mutandis.

As the skilled artisan will appreciate, the term "specific" is used to indicate that other compounds, typically biomolecules, present in a sample do not significantly bind to a ligand (capture compound or detector compound) of the present invention; as will be understood by the skilled person, this does not exclude binding of chemical compounds to regions of the capture compound or detector compound molecule not involved in interaction with the analyte, the specifier, or the tag serving as the functional moiety moderating the binding to a solid phase.

Moreover, the present invention relates to a method for improving the specificity
 (i) of an indirect immunoassay for determining an analyte, comprising replacing at least 10%, in an embodiment, at least 25%, in a further embodiment, at least 40%, in a further embodiment, at least 45%, in a further embodiment, about 50% of a capture compound by a non-identical capture compound, wherein the capture compound replaced competes in binding to said analyte with the capture compound introduced; or
 (ii) of a double-antigen sandwich immunoassay for determining an analyte, comprising replacing at least 50%, in an embodiment, at least 75%, in a further embodiment, at least 90%, in a further embodiment, about 100% of a capture compound by a non-identical capture compound, wherein the capture compound replaced competes in binding to said analyte with the capture compound introduced and wherein said least one capture compound and at least one detector compound are non-identical ligands of said analyte, or
 comprising replacing at least 50%, in an embodiment, at least 75%, in a further embodiment, at least 90%, in a further embodiment, about 100% of a detector compound by a non-identical detector compound, wherein the detector compound replaced competes in binding to said analyte with the detector compound introduced, or of a detector compound and wherein said least one capture compound and at least one detector compound are non-identical ligands of said analyte.

Typically, the fraction of capture compound or detector compound replaced will be selected such that a measurable effect of the replacement can be expected theoretically. As will be understood by the skilled person, expectation of a measurable effect will depend on the number of non-identical ligands used for replacement. E.g. if in the assay after improvement three instead of one capture compounds are used, it is preferred that e.g. 66% of initial capture compound are replaced. As a general rule, it is envisaged that the fraction of a given capture compound or detector compound is $(100\%/n)\pm50\%$, with n=(number of non-identical capture compounds or detector compounds used in an assay). In another embodiment, a fraction of $(100\%/n)\pm20\%$ is used. As will be understood by the skilled person, the sum of fractions used will add up to 100%. Thus, in an embodiment, the fraction of capture compound or detector compound replaced is of from 10% to 90%, in an embodiment, of from 25% to 75%, in a further embodiment, of from 40% to 60%, in a further embodiment, about 50%.

Furthermore, the present invention relates to a kit for detecting an analyte in a sample, comprising
 (i) at least two non-identical capture compounds for said analyte, wherein said capture compounds compete in binding to said analyte; or
 (ii) at least two non-identical detector compounds for said analyte, wherein said detector compounds compete in binding to said analyte.

In an additional embodiment, the invention relates to a kit for detecting an analyte in a sample, comprising
 (i) at least two non-identical capture compounds for said analyte, wherein said capture compounds compete in binding to said analyte, and
 (ii) a specifier, wherein said specifier competes in binding to said capture compounds with said analyte.

The term "kit", as used herein, refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention is to be used for practicing the methods referred to herein above. It is, in an embodiment, envisaged that all components are provided in a ready-to-use manner for practicing the methods referred to above. Further, the kit, in an embodiment, contains instructions for carrying out said methods. The instructions can be provided by a user's manual in paper- or electronic form. For example, the manual may comprise instructions for interpreting the results obtained when carrying out the aforementioned methods using the kit of the present invention. In an embodiment, the kit for detecting an analyte in a sample, comprising at least two non-identical capture compounds of the invention further comprises at least two non-identical detector compounds, wherein said detector compounds compete in binding to said analyte, and wherein said capture compounds do not compete with said detector compounds in binding to said analyte. In a further embodiment, the kit further comprises a solid support for immobilizing said capture compounds or for immobilizing an analyte.

In an embodiment, of from 2 to 10 capture compounds for said analyte, in an embodiment of from 2 to 5 capture compounds for said analyte, in an embodiment of from 2 to 4 capture compounds, in an embodiment of from 2 to 3 capture compounds for said analyte are comprised in said kit. In a further embodiment, of from 2 to 10 detector compounds for said analyte, in an embodiment of from 2 to 5 detector compounds for said analyte, in an embodiment of from 2 to 4 detector compounds, in an embodiment of from 2 to 3 detector compounds for said analyte are comprised in said kit.

Also, the present invention relates to a device for determining an analyte in a sample, comprising
 (i) at least two non-identical capture compounds for said analyte, wherein said capture compounds compete in binding to said analyte; or
 (ii) at least two non-identical detector compounds for said analyte, wherein said detector compounds compete in binding to said analyte, and optionally means for determining an optical or/and enzymatic property of an indicator comprised in said detector compounds.

The term "device", as used herein, relates to a system of means comprising at least the aforementioned means operatively linked to each other as to allow the determination. Typical means for determining the amounts of an analyte, and means for carrying out the determination are disclosed above in connection with the methods of the invention. How to link the means in an operating manner will depend on the type of means included into the device. In an embodiment, the means are comprised by a single device. Said device may accordingly include (i) an analyzing unit for the measurement of the amount of the analyte in an applied sample and a (ii) computer unit for processing the resulting data for the evaluation. Typical means for detection are disclosed in connection with embodiments relating to the method of the invention above. In such a case, the means are operatively linked in that the user of the system brings together the result of the determination of the optically or/and electrochemically determinable property of an indicator and the of the analyte due to the instructions and interpretations given in a manual, or said instructions and interpretations are comprised in an executable program code comprised in the device, such that, as a result of determination, an amount or concentration of analyte in the sample applied is output to the user. The person skilled in the art will realize how to link the means without further ado. Typical devices are those which can be applied without the particular knowledge of a specialized technician, e.g., test stripes or electronic devices which merely require loading with a sample. The results may be given as output of raw data which need interpretation by a technician. In an embodiment, the output of the device is, however, processed, i.e. evaluated, raw data, the interpretation of which does not require a technician. Further typical devices comprise the analyzing units/devices (e.g., biosensors, arrays, solid supports coupled to ligands specifically recognizing the peptide, Plasmon surface resonance devices, NMR spectrometers, mass-spectrometers etc.) or evaluation units/devices referred to above in accordance with the method of the invention.

In an embodiment, of from 2 to 10 capture compounds for said analyte, in an embodiment of from 2 to 5 capture compounds for said analyte, in an embodiment of from 2 to 4 capture compounds, in an embodiment of from 2 to 3 capture compounds for said analyte are comprised in said device. In a further embodiment, of from 2 to 10 detector compounds for said analyte, in an embodiment of from 2 to 5 detector compounds for said analyte, in an embodiment of from 2 to 4 detector compounds, in an embodiment of from 2 to 3 detector compounds for said analyte are comprised in said device.

Moreover, the present invention relates to a composition comprising (i) at least two non-identical capture compounds for an analyte indicative of disease, wherein said capture compounds compete in binding to said analyte; or (ii) at least two non-identical detector compounds for an analyte indicative of disease, wherein said detector compounds compete in binding to said analyte; for use in diagnosis.

The term "composition", as used herein, refers to any composition formulated in solid, liquid or gaseous form. Said composition comprises the compounds of the invention, optionally together with suitable auxiliary compounds such as diluents or carriers or further ingredients. Suitable diluents and/or carriers depend on the purpose for which the composition is to be used and on the other ingredients. The person skilled in the art can determine such suitable diluents and/or carriers without further ado. In an embodiment, the composition for use in diagnosis comprising at least two non-identical capture compounds of the invention further comprises at least two non-identical detector compounds, wherein said detector compounds compete in binding to said analyte, and wherein said capture compounds do not compete with said detector compounds in binding to said analyte.

The term "diagnosis" as used herein refers to an assessment of the probability according to which a subject is suffering or will suffer from a disease or condition. As will be understood by those skilled in the art, such an assessment is usually not intended to be correct for 100% of the subjects to be diagnosed. The term, however, requires that a statistically significant portion of subjects can be correctly diagnosed to suffer from the disease or condition. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the diagnosis will be correct for at least 60%, at least 70%, at least 80%, or at least 90% of the subjects of a given cohort or population. Typical conditions to be diagnosed are, e.g. fertility status or pregnancy. Typical diseases to be diagnosed are, e.g. prevalent or previous infection with a pathogen, e.g. a virus, hyper- or hypothyroidism, vitamin deficiency and the like.

Moreover, the present invention relates to the use of a composition comprising (i) a first and a second capture compound, wherein said first and second capture compounds are non-identical capture compounds, and wherein said capture compounds compete in binding to said analyte, or (ii) a first and a second detector compound, wherein said first and second detector compounds are non-identical detector compounds, and wherein said detector compounds compete in binding to said analyte; for determining an analyte in a sample.

Summarizing the findings of the present invention, the following embodiments are disclosed:

Embodiment 1. A method for determining an analyte in a sample suspected to comprise said analyte, comprising
  a) contacting with said sample at least a first and a second capture compound for said analyte, wherein said first and second capture compounds are non-identical capture compounds, and wherein said capture compounds compete in binding to said analyte;
  b) contacting said capture compounds contacted with said sample
  (i) with a detector compound, wherein said detector compound competes in binding to said analyte with said capture compounds; or
  (ii) with a specifier, wherein said specifier competes in binding to said capture compounds with said analyte;
  c) determining the amount of complexes comprising
  (i) said detector compound and a capture compound, or
  (ii) said specifier and a capture compound; and
  d) determining said analyte in a sample based on the result of step c).

Embodiment 2. The method of embodiment 1, wherein competing in binding to a molecule is binding to essentially the same or to the same substructure of said molecule, in an embodiment, wherein competing in binding to said analyte is binding to essentially the same or to the same substructure of said analyte, in an embodiment, wherein competing in binding to said capture compounds is binding to essentially the same or to the same substructure of said at least one, in an embodiment, all capture compounds.

Embodiment 3. The method of embodiment 1 or 2, wherein said non-identical capture compounds are biological molecules, in an embodiment, biological macromolecules, in a further embodiment, polypeptides.

Embodiment 4. The method of any one of embodiments 1 to 3, wherein said two non-identical capture compounds are variants of a viral polypeptide, in an embodiment, of a viral capsid polypeptide.

Embodiment 5. The method of any one of embodiments 1 to 4, wherein said two non-identical capture compounds are variants of a Hepatitis virus capsid polypeptide, in an embodiment, of a Hepatitis B virus (HB) capsid polypeptide, in a further embodiment, of a HB core (HBc) antigen.

Embodiment 6. The method of any one of embodiments 1 to 2, wherein said second capture compound is a variant of an antibody being the first capture compound; or wherein said first and second capture compounds are antibodies recognizing essentially the same epitope.

Embodiment 7. The method of any one of embodiments 1 to 6, wherein said second capture compound is derived or derivable from said first capture compound by at least one of:
  (i) introducing at least one amino acid exchange into the amino acid sequence of said first capture compound,
  (ii) producing said second capture compound in a different cellular background as compared to said first capture compound,
  (iii) removing or preventing glycosylation of said second capture compound as compared to said first capture compound,
  (iv) purifying said second capture compound by different means and/or by a different method as compared to said first capture compound,
  (v) denaturing and/or refolding said second capture compound under different conditions as compared to said first capture compound, and
  (vi) storing said second capture compound under different conditions as compared to said first capture compound.

Embodiment 8. The method of any one of embodiments 1 to 7, wherein said analyte is a biological macromolecule.

Embodiment 9. The method of any one of embodiments 1 to 8, wherein said analyte is a polypeptide.

Embodiment 10. The method of any one of embodiments 1 to 9, wherein said analyte is an antibody against a viral antigen, in an embodiment, against a viral polypeptide, in a further embodiment, against a viral capsid polypeptide.

Embodiment 11. The method of any one of embodiments 1 to 10, wherein said analyte is an antibody against a Hepatitis virus capsid polypeptide, in an embodiment, against a Hepatitis B virus (HB) capsid polypeptide, in a further embodiment, against a HB core (HBc) antigen.

Embodiment 12. The method of any one of embodiments 9 to 11, wherein the epitopes bound by said capture compounds have at least 3 amino acids in common.

Embodiment 13. The method of any one of embodiments 1 to 12, wherein said determining an analyte is qualitatively or quantitatively determining the amount of said analyte.

Embodiment 14. The method of any one of embodiments 1 to 13, wherein step a) comprises contacting with said sample of from 2 to 10 capture compounds for said analyte, in an embodiment of from 2 to 5 capture compounds for said analyte, in an embodiment of from 2 to 4 capture compounds, in an embodiment of from 2 to 3 capture compounds for said analyte.

Embodiment 15. The method of any one of embodiments 1 to 14, wherein said specifier comprises the substructure of the analyte bound by the capture compounds, bonded to an indicator.

Embodiment 16. The method of any one of embodiments 1 to 15, wherein said specifier is a compound comprising the analyte and an indicator.

Embodiment 17. The method of any one of embodiments 1 to 16 wherein said specifier consists of the analyte covalently bonded to an indicator.

Embodiment 18: The method of any one of embodiments 1 to 17, wherein said capture compounds are not comprised in a polyclonal antiserum, in an embodiment, are not polyclonal antibodies.

Embodiment 19. The method of any one of embodiments 1 to 18, wherein said first and second capture compounds do not compete in binding to an interfering compound.

Embodiment 20. The method of any one of embodiments 1 to 19, comprising the steps of:
  a) contacting with said sample at least a first and a second capture compound for said analyte, wherein said first and second capture compounds are non-identical capture compounds, and wherein said capture compounds compete in binding to said analyte;
  b) contacting said capture compounds contacted with said sample with a specifier, wherein said specifier competes in binding to said capture compounds with said analyte;
  c) determining the amount of complexes comprising said specifier and a capture compound; and
  d) determining said analyte in a sample based on the result of step c).

Embodiment 21. A method for determining an analyte in a sample suspected to comprise said analyte, comprising
  a) contacting said sample to at least a first and a second detector compound for said analyte, wherein said first and second detector compounds are non-identical detector compounds, and wherein said detector compounds compete in binding to said analyte;
  b) binding constituents of said sample including at least said analyte to a solid surface,
  c) determining the amount of complexes comprising a detector compound bound to said solid surface; and
  d) determining said analyte in a sample based on the result of step c).

Embodiment 22. The method of embodiment 22, wherein said analyte comprises an antibody, in an embodiment, is an antibody.

Embodiment 23. The method of any one of embodiments 21 to 22, wherein said detector compound further comprises an indicator.

Embodiment 24. The method of any one of embodiments 15 to 17 or 23, wherein said indicator is a compound having a detectable property, in an embodiment, an optical or/and enzymatic property.

Embodiment 25. The method of any one of embodiments 20 to 24, wherein said first and second detector compound do not compete in binding to an interfering compound.

Embodiment 26. The method of any one of embodiments 20 to 25, wherein step a) is performed after step b).

Embodiment 27. A method for improving the specificity
  (a) of (i) an indirect immunoassay for determining an analyte or (ii) a double-antigen sandwich immunoassay for determining an analyte, comprising:
  replacing at least 10%, in an embodiment, at least 25%, in a further embodiment, at least 40%, in a further embodiment, at least 45%, in a further embodiment, about 50% of a capture compound by a non-identical capture compound, wherein the capture compound replaced competes in binding to said analyte with the capture compound introduced; or (b) of a double-antigen sandwich immunoassay for determining an analyte, comprising:

replacing at least 25%, in an embodiment, at least 40%, in a further embodiment, at least 45%, in a further embodiment, about 50% of a detector compound by a non-identical detector compound, wherein the detector compound replaced competes in binding to said analyte with the detector compound introduced and wherein said least one capture compound and at least one detector compound are non-identical capture compounds of said analyte.

Embodiment 28. The method of any one of embodiments 1 to 27, wherein the chemical structure in said capture compounds and/or said detector compounds binding to said analyte is identical in all of said non-identical capture compounds and/or in all of said non-identical detector compounds.

Embodiment 29. A kit for detecting an analyte in a sample, comprising
  (i) at least two non-identical capture compounds for said analyte, in an embodiment of from 2 to 10 capture compounds for said analyte, in an embodiment of from 2 to 5 capture compounds for said analyte, in an embodiment of from 2 to 4 capture compounds, in an embodiment of from 2 to 3 capture compounds, for said analyte, wherein said capture compounds compete in binding to said analyte; or
  (ii) at least two non-identical detector compounds for said analyte, in an embodiment of from 2 to 10 detector compounds for said analyte, in an embodiment of from 2 to 5 detector compounds for said analyte, in an embodiment of from 2 to 4 detector compounds, in an embodiment of from 2 to 3 detector compounds, for said analyte, wherein said detector compounds compete in binding to said analyte.

Embodiment 30. The kit of embodiment 29, further comprising a solid support for immobilizing said capture compounds or constituents of said sample comprising at least said analyte.

Embodiment 31. A device for determining an analyte in a sample, comprising
  (i) at least two non-identical capture compounds for said analyte, in an embodiment of from 2 to 10 capture compounds for said analyte, in an embodiment of from 2 to 5 capture compounds for said analyte, in an embodiment of from 2 to 4 capture compounds, in an embodiment of from 2 to 3 capture compounds, for said analyte, wherein said capture compounds compete in binding to said analyte; or
  (ii) at least two non-identical detector compounds for said analyte, in an embodiment of from 2 to 10 detector compounds for said analyte, in an embodiment of from 2 to 5 detector compounds for said analyte, in an embodiment of from 2 to 4 detector compounds, in an embodiment of from 2 to 3 detector compounds, for said analyte, wherein said detector compounds compete in binding to said analyte and optionally means for determining an optical or/and enzymatic property of an indicator comprised in said detector compounds.

Embodiment 32. A composition comprising
  (i) at least two non-identical capture compounds for an analyte indicative of disease, wherein said capture compounds compete in binding to said analyte, or
  (ii) at least two non-identical detector compounds for an analyte indicative of disease, wherein said detector compounds compete in binding to said analyte;
for use in diagnosis of disease.

Embodiment 33. Use of
  (i) at least two non-identical capture compounds for an analyte, wherein said capture compounds compete in binding to said analyte; and/or
  (ii) at least two non-identical detector compounds for an analyte, wherein said detector compounds compete in binding to said analyte;
for the manufacture of a diagnostic composition or a diagnostic device.

Embodiment 34. The composition for use of embodiment 32 or use of embodiment 33, wherein said disease is viral hepatitis.

Embodiment 35. Use of a composition comprising (i) a first and a second capture compound, wherein said first and second capture compounds are non-identical capture compounds, and wherein said capture compounds compete in binding to said analyte; or (ii) a first and a second detector compound, wherein said first and second detector compounds are non-identical detector compounds, and wherein said detector compounds compete in binding to said analyte; for determining an analyte in a sample.

Short Description of the Figures

Further optional features and embodiments of the invention will be disclosed in more detail in the subsequent description of embodiments, in an embodiment, in conjunction with the dependent claims. Therein, the respective optional features may be realized in an isolated fashion as well as in any arbitrary feasible combination, as the skilled person will realize. The scope of the invention is not restricted by the disclosed embodiments. The embodiments are schematically depicted in the Figures. Therein, identical reference numbers in these Figures refer to identical or functionally comparable elements.

BRIEF DESCRIPTION OF THE FIGURES

FIG. 1A) In the absence of the analyte, the specifier binds to capture compound 1. FIG. 1B) In the presence of the analyte, the analyte binds to capture compound 1 and prevents the specifier from binding to capture compound 1. FIG. 1C) In the presence of interfering agent 1, having affinity to capture compound 1 (but not to capture compound 2), interfering agent 1 binds to capture compound 1, thus preventing the specifier from binding. FIG. 1D) In the presence of interfering agent 2, having affinity to capture compound 2 (but not to capture compound 1), interfering agent 2 does not bind to capture compound 1, thus permitting the specifier to bind to capture compound 1. Conversely, FIG. 1E) interfering agent 1, having affinity to capture compound 1 (but not to capture compound 2), does not bind to capture compound 2, thus permitting the specifier to bind to capture compound 2; and FIG. 1F) interfering agent 2 does bind to capture compound 2, thus preventing the specifier from binding. (FIG. 1G) and 1H)) in case capture compound 1 and 2 are used e.g. at a 1:1 ratio, the false signal reduction induced by interfering agent 1 or interfering agent 2 will be reduced to approximately 50%.

FIG. 2A) in the absence of the analyte (α-HBc antibody), both, Ru-conjugated and bio-conjugated α-HBc antibodies can bind to HBc added to the assay mixture. Via the bio-strip-interaction, the complex is bound to a solid support and after washing, a signal generated from the Ru-conjugation can be measured. FIG. 2B) in the presence of the analyte (α-HBc antibody), the α-HBc-bio antibody and Ru-conjugated antibody are prevented from binding to HBc added to the assay mixture, thus preventing binding of a complex to the solid support. Accordingly, after washing, no signal can be generated from the Ru-complex, since this will be washed off. In FIGS. 2A & 2B, HBc as well as the α-HBc-bio conjugate are part of the capture compound complex.

FIG. 3A) in the absence of analyte, no analyte is bound to capture compound 1 (or 2) fixed on a solid support and, thus, the detector compound will be washed away in washing steps. FIG. 3B) in the presence of the analyte, e.g. an antibody, the analyte binds to capture compound 1 and to the detector compound, thus mediating binding of the detector compound to the solid surface. FIG. 3C) in the presence of interfering agent 1, which binds to capture compound 1 and to the detector compound, but not to capture compound 2, the detector compound becomes fixed to the solid support via the interaction with interfering agent 1. FIG. 3D) in the presence of interfering agent 2, which binds to capture compound 2 and to the detector compound, but not to capture compound 1, the detector compound is not fixed to the solid support via interfering agent 1. Conversely, FIG. 3E) in the presence of interfering agent 1, the detector compound is not fixed to the solid support via the interaction with interfering agent 2; and FIG. 3F) in the presence of interfering agent 2, the detector compound will be fixed to the solid support via capture compound 2. (FIG. 3G) and 3H)) in case capture compound 1 and 2 are used e.g. at a 1:1 ratio, the false signal increase induced by interfering agent 1 or interfering agent 2 will be reduced to approximately 50%. A scheme could mutatis mutandis be drawn for the use of two non-identical detector compounds.

EXAMPLES

Example 1

Figure 1A:
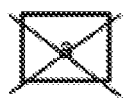
FIGS. 1A-1H schematically indicate the principle of the present invention as applied to a competitive assay; a: analyte, s: specifier, c1: capture compound 1, c2: capture compound 2, i1: interfering agent 1, i2: interfering agent 2.
Figure 1B:
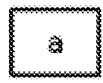
Figure 1C:
Figure 1D:
Figure 1E:
Figure 1F:
Figure 1G:
Figure 1H:
Figure 2A:
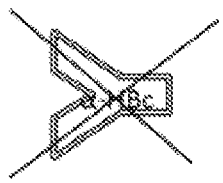
FIGS. 2A & 2B schematically show the test principle of a competitive test for anti-Hepatitis core (HBc) antigen antibodies. HBc: Hepatitis B core antigen; α-HBc: anti-HBc antigen antibody; the non-conjugated α-HBc antibody depicted with a double circumference is an antibody potentially present in a sample from a patient, the conjugated antibodies depicted with a single circumference are α-HBc antibodies added during the assay; conjugation is either with Ru: Ruthenium-complex, or bio: biotin; strip: streptavidin-coating of a solid support.
Figure 2A:
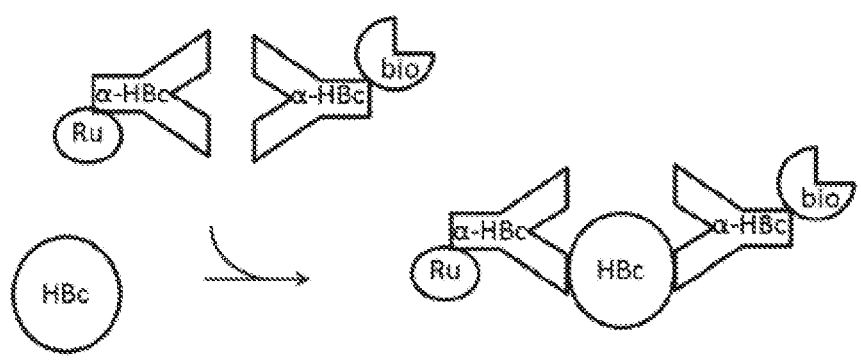
Figure 2A:
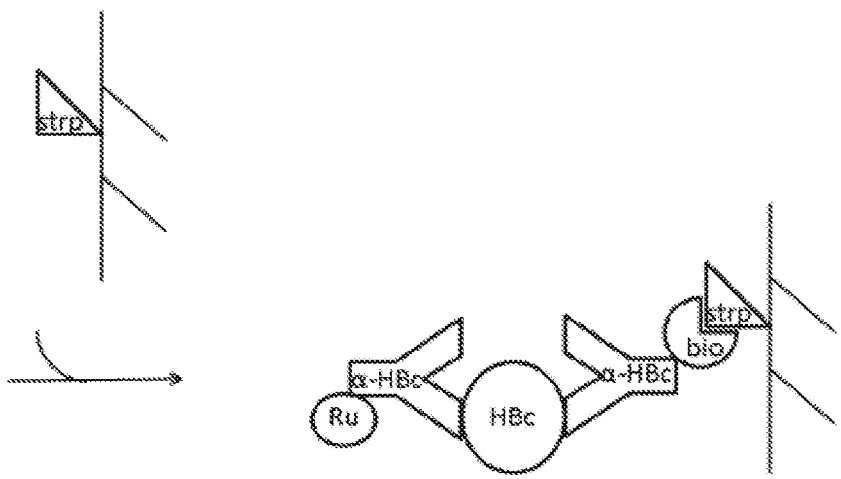
Figure 2B:
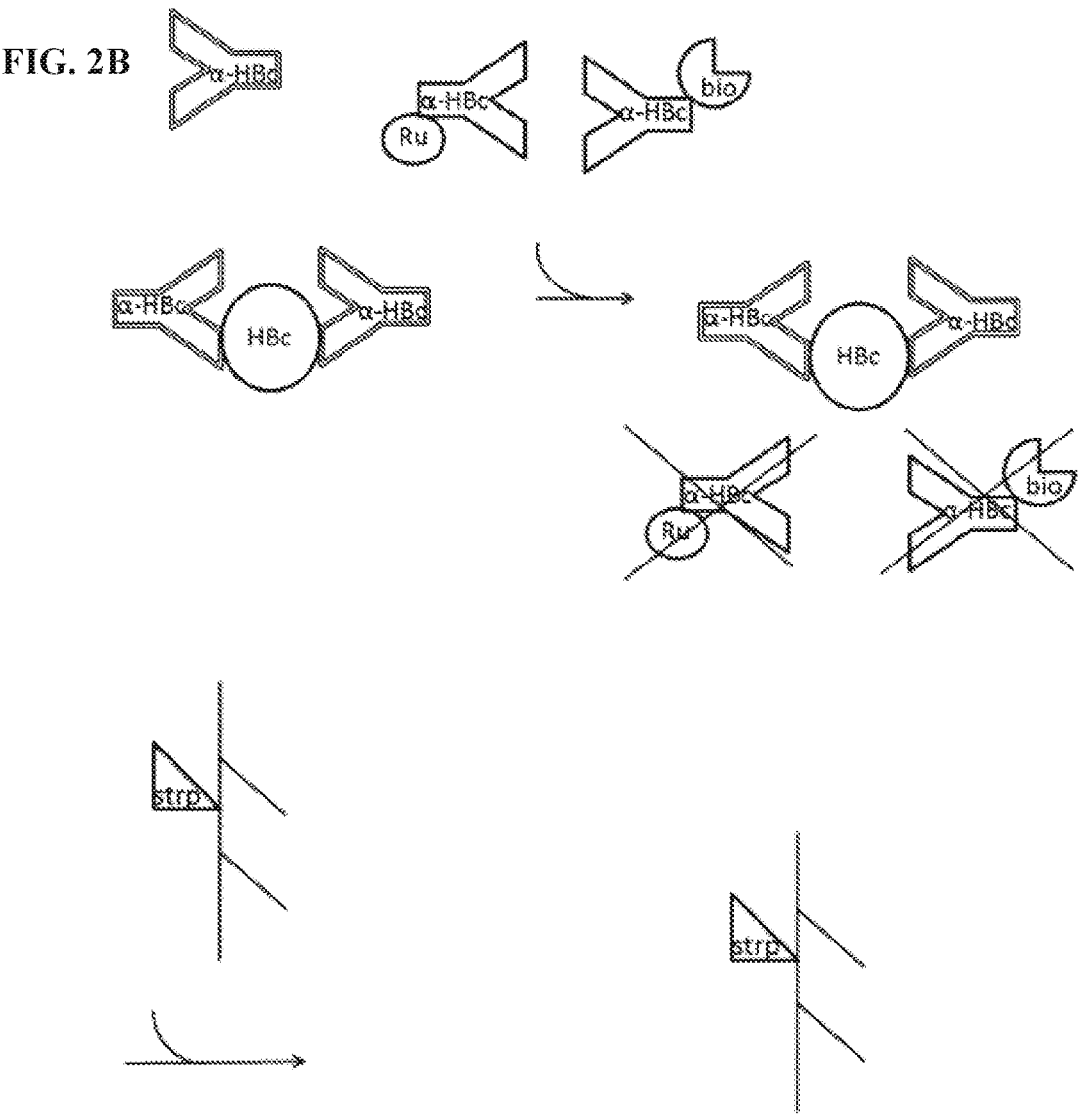
Figure 3A:
FIGS. 3A-3H schematically indicates the principle of the present invention as applied to a double-antigen sandwich (DAGS) format. a: analyte, d: detector compound, c1: capture compound 1, c2: capture compound 2, i1: interfering agent 1, i2: interfering agent 2.
Figure 3B:
Figure 3C:
Figure 3D:
Figure 3E:
Figure 3F:
Figure 3F:
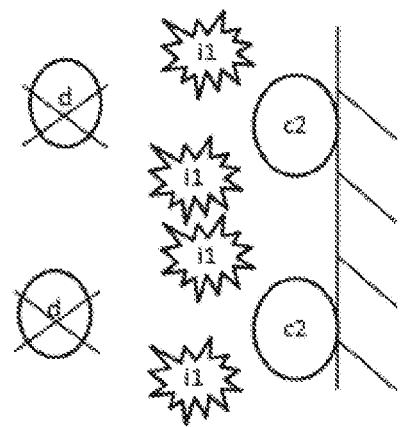
Figure 3F:
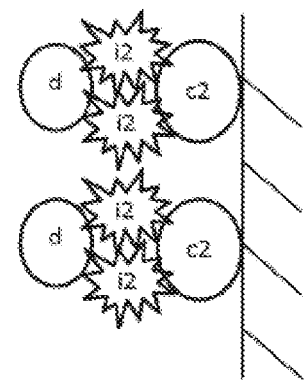
Figure 3G:
Figure 3H:
Figure 3H:
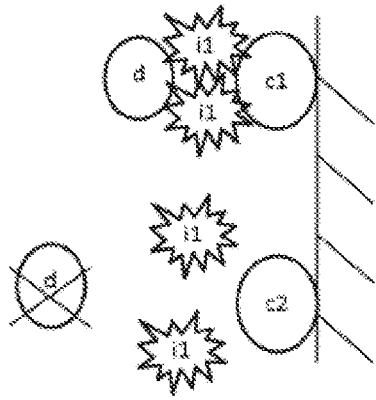
Figure 3H:
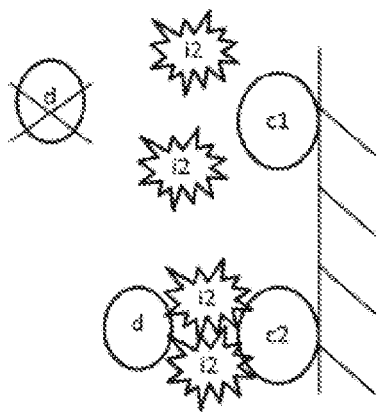

Cloning and Purification of Recombinant Hepatitis B Core Antigen

The synthetic gene encoding the Hepatitis B core antigen (HBcAg) was purchased from Eurofins MWG Operon (Ebersberg, Germany). On the basis of the pET24a expression plasmid of Novagen (Madison, WI, USA) the following cloning steps were performed. The vector was digested with BamH1 and Xho1 and a cassette comprising the HBcAg was inserted. The insert of the resulting plasmid was sequenced and found to encode the desired protein. The amino acid sequence of the resulting protein is shown in the sequence protocol of the present invention. The recombinant HBcAg did not contain a C-terminal hexahistidine tag.

The recombinant HBcAg was purified according to the following protocol. $E.\ coli$ BL21 (DE3) cells harboring the expression plasmid were grown in LB medium plus kanamycin (30 µg/ml) to an OD600 of 1, and cytosolic overexpression was induced by adding isopropyl-β-D-thiogalactosid (IPTG) to a final concentration of 1 mM at a growth temperature of 37° C. 4 hours after induction, cells were harvested by centrifugation (20 min at 5000×g), frozen and stored at −20° C. For cell lysis, the frozen pellet was resuspended in 25 mM sodium phosphate pH 8.5, 6 mM $MgCl_2$, 10 U/ml Benzonase®, 1 tablet Complete® and 1 tablet Complete® EDTA-free per 50 ml of buffer (protease inhibitor cocktail) and the resulting suspension was lysed by high pressure homogenization. The crude lysate was centrifuged and the HBcAg in the supernatant was precipitated with ammonium sulfate (35% w/v). After additional centrifugation the precipitate was resuspended and dialyzed against a phosphate buffer followed by a heating step (70° C. for 30 minutes). After centrifugation the clear supernatant was applied onto a Toyopearl DEAE 650-11 column (from Tosoh Bioscience) pre-equilibrated in 25 mM potassium phosphate pH 7. The protein was then eluted by applying a gradient up to a potassium chloride concentration of 500 mM. Finally, the protein was subjected to size exclusion chromatography (S400) and the protein-containing fractions were pooled.

Example 2

Immunoassay for Detecting Anti-HBc Antibodies in a Competitive Test Format

Serum samples from a panel of healthy blood donors were analyzed in a competitive Anti-HBc ECLIA (Electrochemiluminescence Immunoassay) for the presence of anti-HBc antibodies in automated Cobas e® analyzers (Roche Diagnostics GmbH). Cobas E® and Elecsys® are registered trademarks of the Roche group. The samples were tested negative for Anti-HBc with at least one CE-marked Anti-HBc assay that is different from the Elecsys® Anti-HBc assay and which is commercially available.

In the assay, serum is reacted with HBc. After addition of biotinylated antibodies and ruthenium complex (Tris(2,2'-bipyridyl)ruthenium(II)-complex; (Ru(bpy)32+)-labeled antibodies, both specific for HBcAg, together with streptavidin-coated microparticles, the still-free binding sites on the HBc-antigens become occupied. The entire complex becomes bound to the solid phase via interaction of biotin and streptavidin. After removal of unbound substances, a voltage is applied to the electrode and induces chemiluminescent emission at 620 nm after excitation at a platinum electrode which is measured by a photomultiplier.

High measured values indicate binding of biotinylated antibodies and ruthenium complex-labeled antibodies added and, thus, absence of anti-HBc antibodies in the sample. In the presence of anti-HBc antibodies in the sample these antibodies compete with both types of assay specific antibodies for binding to the antigen HBcAG leading to reduced light emission at 620 nm after excitation at a platinum electrode. The signal output is in arbitrary light units.

Accordingly, samples having a measured value of higher than the cut-off index 1.0 are considered non-reactive, whereas samples having a measured lower than or equal to the cut-off index 1.0 are considered reactive.

Based on the competitive Elecsys® Anti-HBc assay format three different HBcAg settings were tested. "HBcAg X" refers to an antigen comprising SEQ ID NO:2; "HBcAg Y" refers to an antigen comprising SEQ ID NO:1. Only the antigen setting was modified, all other reagent and conditions remained unchanged. The results of true positive (infected) samples was not affected by applying a combination of HBcAg X and Y as first and second capture compound (data not shown). Table 1 relates only to discrepant (=false) positive results of the sample panel. The three different settings were as follows:

A) HBcAg X is used as target in the competitive Anti-HBc assay.
B) HBcAg Y (slightly different from HBcAg X) is used as target in the competitive Anti-HBc assay.
C) A combination of HBcAg X and HBcAg Y are used together as target in the competitive anti-HBc assay Table 1 shows the results of a competitive Anti-HBc-ECLIA (Electrochemiluminescence Immunoassay). Commercially available sera (Bavarian Red Cross) negative for antibodies against HBc antigen were used as samples. Table 1 lists only those results with discrepant findings. Different HBcAG showed individual patterns of discrepant positive Anti-HBc results. When two different preparations of HBc-antigen (HBcAG) were used, 11 samples were tested (false–) positive (reactive) when HBcAG X was used, 7 samples tested (false–) positive only when the second HBcAG Y was used, and 2 samples tested (false)– positive with both HBcAG X and with HBcAG Y. In contrast, when a 1:1 mixture of both antigens, i.e. HBcAG X and HBcAG Y was used, only 5 of these 18 samples tested positive, decreasing the number of false-positive tests by more than 3-fold. In detail, the number of samples tested false-positive using HBcAGX only, was reduced from 11 to 3 and the number of samples tested false-positive using HBcAGY only, was reduced from 9 to 5 when said 1:1 mixture of both antigens (HBcAG X and HBcAG Y) was used. As expected, the two samples tested false-positive with both antigens (Samples No. 2942 and 3657), also tested false-positive with the mixture.

As a consequence, the specificity of this competitive immunoassay was increased when at least two slightly different HBc antigens were applied as a mixture.

By applying the principle of using two slightly different first and second capture compounds for an analyte in a method based on a competitive test format the specificity can be considerably increased, i.e. false positive results can be avoided to a considerable extent.

TABLE 1

Results of a competitive Anti-HBC ECLIA (Electrochemiluminescence Immunoassay),

| Interpretation | | HBcAG X reactive COI ≤ 1.0 non-reactive COI > 1.0 | HBcAG Y COI ≤ 1.0 COI > 1.0 | HBcAG Mix X + Y COI ≤ 1.0 COI > 1.0 |
|---|---|---|---|---|
| | Sample No. | COI | COI | COI |
| Anti-HBcAG X interference | 1984 | 0.234* | 2.19 | 1.19 |
| | 2942 | 0.463* | 0.462* | 0.396* |
| | 3180 | 0.582* | 1.37 | 0.976* |
| | 3633 | 0.639* | 2.17 | 1.29 |
| | 3470 | 0.788* | 2.26 | 1.38 |
| | 3784 | 0.820* | 2.17 | 1.47 |
| | 2426 | 0.865* | 1.53 | 1.06 |
| | 3657 | 0.878* | 0.984* | 0.858* |
| | 3976 | 0.891* | 2.34 | 1.41 |
| | 2423 | 0.927* | 2.16 | 1.52 |
| | 2905 | 0.990* | 2.22 | 1.51 |
| Anti-HBcAG Y interference | 2858 | 1.66 | 0.185* | 0.941* |
| | 3813 | 1.59 | 0.311* | 1.07 |
| | 1344 | 1.39 | 0.428* | 0.910* |
| | 2038 | 2.05 | 0.473* | 1.21 |
| | 2898 | 2.03 | 0.754* | 1.38 |
| | 1529 | 1.83 | 0.800* | 1.34 |
| | 2263 | 1.56 | 0.840* | 1.20 |
| Anti-HBc negative | 2243 | 1.84 | 2.26 | 2.09 |
| | 2269 | 1.94 | 2.26 | 2.04 |
| | 2155 | 2.02 | 2.26 | 2.13 |
| | 1311 | 1.98 | 2.26 | 2.08 |
| | 1065 | 2.01 | 2.26 | 2.26 |
| * Discrepant positive samples [n] | | 11 | 9 | 5 |

COI: Cut-off index

The invention claimed is:

1. A kit for detecting an analyte in a sample, comprising
at least two non-identical capture compounds for said analyte, or
at least two non-identical detector compounds for said analyte,
wherein said at least two non-identical capture compounds or detector compounds are non-identical polypeptides differing in at least one property selected from the group consisting of amino acid sequence, glycosylation, three-dimensional folding and/or conformation, and length of polypeptide chain, and
wherein said at least two non-identical capture compounds or detector compounds compete in binding to said analyte.

2. The kit of claim 1, wherein said at least two non-identical capture compounds or said at least two non-identical detector compounds comprise the same analyte binding domain.

3. The kit of claim 1, wherein said kit comprises at least two non-identical capture compounds.

4. The kit of claim 3, wherein said at least two non-identical capture compounds have amino acid sequences sharing at least 70% sequence identity.

5. The kit of claim 3, wherein said at least two non-identical capture compounds are bound to a solid surface or are adapted to be bound to a solid surface.

6. The kit of claim 3, wherein said kit further comprises at least one antibody forming capture complexes with said at least two capture compounds.

7. The kit of claim 6, wherein said at least one antibody is bound to a solid surface or is adapted to be bound to a solid surface.

8. The kit of claim 3, wherein said at least two non-identical capture compounds are direct ligands of said analyte.

9. The kit of claim 1, wherein said kit comprises from 2 to 10 capture compounds for said analyte, from 2 to 5 capture compounds for said analyte, from 2 to 4 capture compounds for said analyte, or from 2 to 3 capture compounds for said analyte.

10. The kit of claim 3, wherein said kit further comprises a specifier.

11. The kit of claim 10, wherein said specifier comprises at least a portion of the analyte bound by the at least two non-identical capture compounds, bonded to an indicator.

12. The kit of claim 10, wherein the specifier consists of the analyte covalently bonded to an indicator.

13. The kit of claim 1, wherein said kit comprises at least two non-identical detector compounds, said detector compounds each comprising said analyte binding domain and an indicator.

14. The kit of claim 13, wherein said at least two non-identical detector compounds have amino acid sequences sharing at least 70% sequence identity.

15. The kit of claim 13, wherein said at least two non-identical detector compounds comprise the same indicator.

16. The kit of claim 13, wherein said indicator has a detectable property selected from the group consisting of an optical property, an enzymatic property, and a property of emitting radioactivity.

17. The kit of claim 13, wherein said at least two non-identical detector compounds are direct ligands of said analyte.

18. The kit of claim 1, wherein said kit comprises from 2 to 10 detector compounds for said analyte, from 2 to 5 detector compounds for said analyte, from 2 to 4 detector compounds for said analyte, or from 2 to 3 detector compounds for said analyte.

19. The kit of claim 1, wherein said at least two non-identical capture compounds or said at least two non-identical detection compounds do not compete in binding to an interfering compound.

20. The kit of claim 1, wherein a first capture compound or a first detector compound comprises an amino acid sequence at least 70% identical to SEQ ID NO:1, and/or wherein a second capture compound or a second detector compound comprises an amino acid sequence at least 70% identical to SEQ ID NO:2.

* * * * *